US00PP19206P2

(12) United States Plant Patent
Noack

(10) Patent No.: US PP19,206 P2
(45) Date of Patent: Sep. 9, 2008

(54) GROUND COVER ROSE PLANT NAMED 'NOA168098F'

(50) Latin Name: *Rosa hybrida*
Varietal Denomination: NOA168098F

(76) Inventor: Reinhard Noack, Im Fenne 54, Gütersloh (DE), 33334

( * ) Notice: Subject to any disclaimer, the term of this patent is extended or adjusted under 35 U.S.C. 154(b) by 0 days.

(21) Appl. No.: 11/822,612

(22) Filed: Jul. 9, 2007

(51) Int. Cl.
*A01H 5/00* (2006.01)

(52) U.S. Cl. ..... Plt./108

(58) Field of Classification Search ..... Plt./108
See application file for complete search history.

(56) References Cited
U.S. PATENT DOCUMENTS

PP17,877 P3 * 7/2007 Meilland ..... Plt./108

* cited by examiner

*Primary Examiner*—Wendy C. Haas

(57) ABSTRACT

A new and distinct variety for Ground Cover Rose plant is provided which forms in sprays attractive long-lasting red-purple blossoms which are lacking in fragrance with yellow pollen and reproductive organs commonly being visible at the center and which commonly display very good heat resistance and color stability upon aging. The new variety exhibits a dense, compact, and spreading growth habit. The foliage is green and very glossy on the upper surface and contrasts well with the red-purple blossom coloration. The surfaces of leaves commonly are somewhat curled and partially closed. The blossom petals commonly detach cleanly upon full maturity. The plant propagates well from cuttings and by budding. Excellent resistance to Blackspot; Powdery Mildew, Downey Mildew, and Rust are displayed, and the plant is particularly well suited for growing as an ornamental ground cover in the landscape.

2 Drawing Sheets

Figure 1:
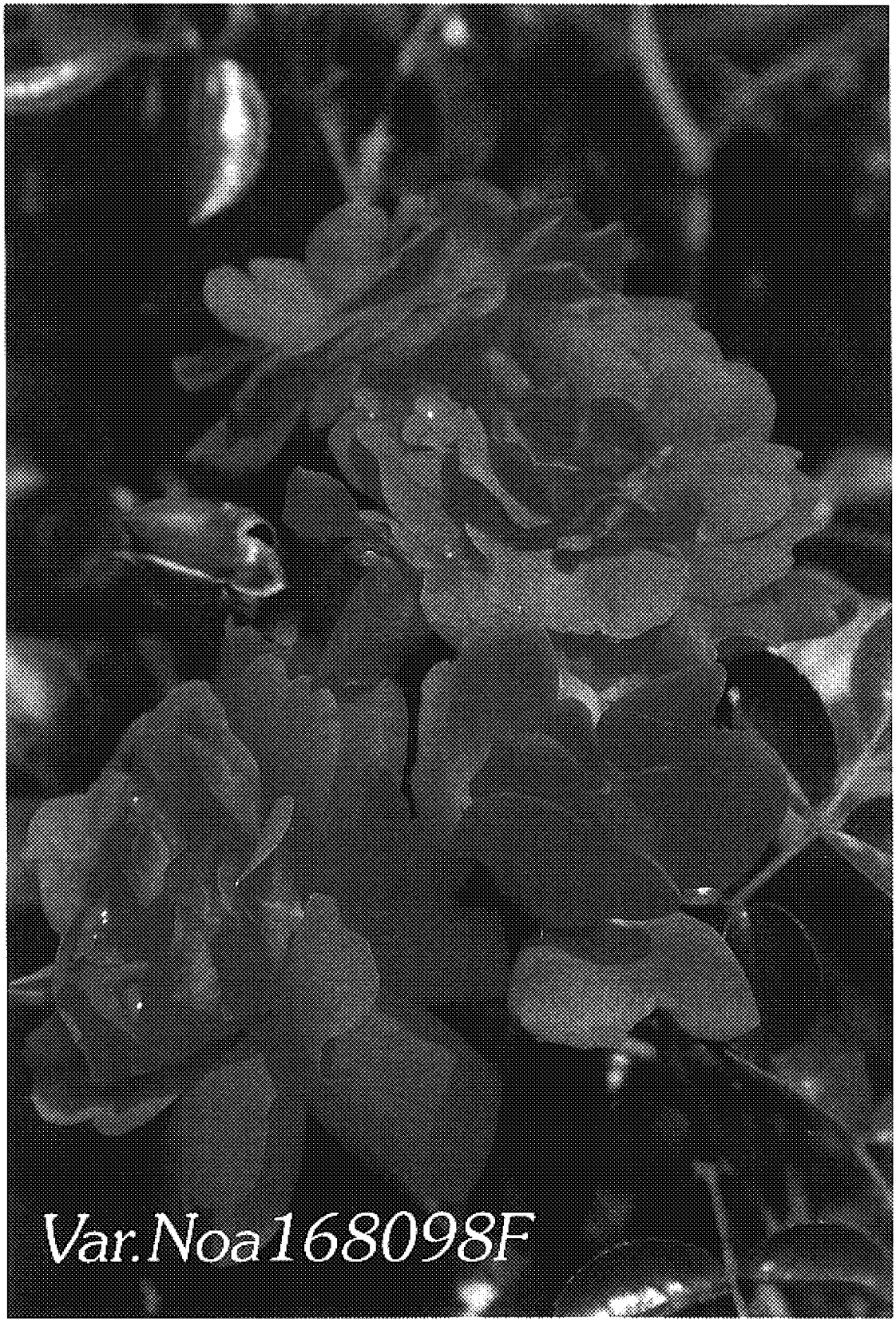

Botanical/commercial classification: *Rosa hybrida*/ Ground Cover Rose Plant.
Varietal denomination: cv. 'NOA168098F'.

SUMMARY OF THE INVENTION

Ground Cover rose plants are known and are being used to advantage in an increasing number of landscape plans and home gardens. However, there remains a need for additional varieties of Ground Cover roses with the demand being the greatest for those having highly attractive blossoms in combination with good disease resistance.

The new variety of *Rosa hybrida* Ground Cover or Shrub rose plant of the present invention was created in Gütersloh, Germany, by artificial pollination wherein two parents were crossed which previously had been studied in the hope that they would contribute the desired characteristics. The female parent (i.e., the seed parent) was the 'Korimro' variety (non-patented in the United States). The 'Korimro' variety is marketed under the IMMENSEE trademark. The male parent (i.e., the pollen parent) was an unnamed and unreleased seedling maintained by Noack Rosen at Gütersloh, Germany (non-patented in the United States). The parentage of the new variety can be summarized as follows:

'Korimro'×Unnamed Seedling.

The seeds resulting from the above pollination were sown and small plants were obtained which physically and biologically differ from each other. Selective study resulted in the identification of a single plant to the new variety.

It is found that the new variety of Ground Cover rose plant possesses the following combination of characteristics:

(a) forms in sprays attractive long-lasting red-purple blossoms which are lacking in fragrance with yellow pollen and reproductive organs commonly being visible at the center and which commonly display very good heat resistance and color stability upon aging,
(b) exhibits a dense, compact, and spreading growth habit,
(c) abundantly forms attractive very glossy green foliage that contrasts well with the red-purple blossoms wherein the surfaces of the leaflets commonly are somewhat curled and partially closed,
(d) exhibits excellent disease resistance with respect to Blackspot, Powdery Mildew, Downey Mildew, and Rust, and
(e) is particularly well suited for growing as attractive ornamentation in the landscape.

The new variety meets the needs of the horticultural industry and can be grown to advantage as attractive ornamentation in parks, gardens, public areas, and residential landscapes.

The new variety of the present invention can be readily distinguished from its ancestors. More specifically, the 'Korimro' female parent forms light pink to near white single blossoms wherein the coloration is substantially different when compared to the new variety of the present invention.

The new variety of the present invention beginning in 1998 has been asexually reproduced by the rooting of cuttings, and by budding. Such asexual reproduction as performed at Gütersloh, Germany, has demonstrated that the characteristics of the new variety are firmly fixed and stable and are strictly transmissable from one generation to another. The new variety asexually reproduces in a true to type manner from one generation to another.

The new variety of the present invention has been named 'NOA168098F'.

BRIEF DESCRIPTION OF THE PHOTOGRAPHS

The accompanying photographs show as nearly true as it is reasonably possible to make the same, in color illustrations of this character, typical specimens of the new variety while growing outdoors. The illustrated rose plants were photographed during June, 2006, while growing in a field at Gütersloh, Germany. Such plants had been budded approximately one and one-half years earlier.

FIG. 1 illustrates a close view of the attractive bright red-purple blossoms and very glossy green foliage of the new variety.

Figure 2:
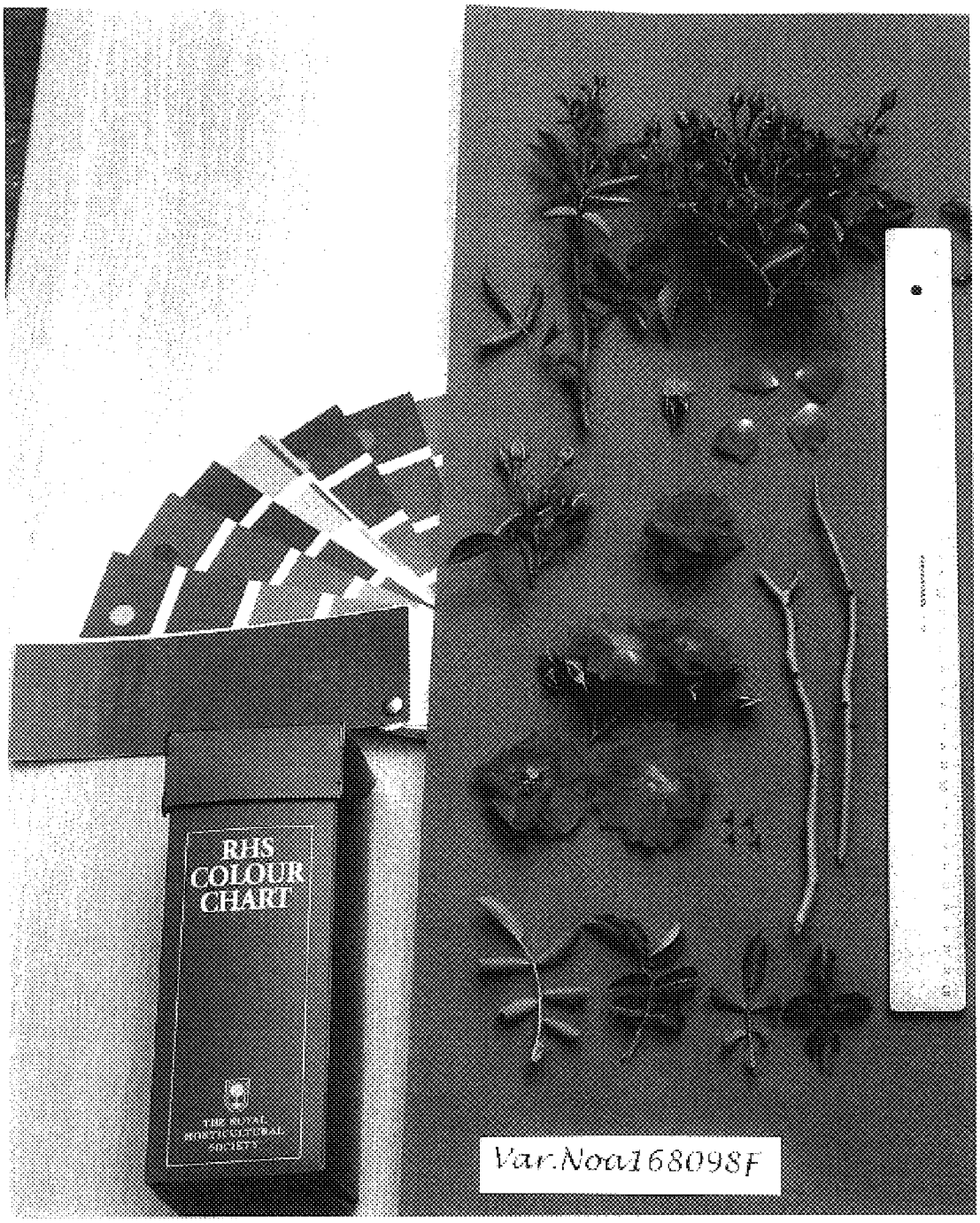

FIG. 2 illustrates at the right typical plant parts of the new variety of the present invention wherein a ruler showing centimeters is included for size comparison. At the top and bottom, the upper and under surfaces of typical leaves are shown with clusters of foliage with unopened floral buds being present at the top. Toward the center are shown typical floral petals, a floral receptacle, additional floral buds, flowers in various stages of opening, floral stems, and thorns. At the left are included pages from R.H.S. Colour Chart for color comparison.

DETAILED DESCRIPTION

The chart used in the identification of the colors is that of The Royal Horticultural Society (R.H.S. Colour Chart) of London, England. Color terminology in common terms sometimes is included as an aid to the reader. Such color terminology is to be accorded its customary dictionary significance. The description is based on the observation of typical specimens of the new variety while growing outdoors during June at Gütersloh, Germany.

Class: Ground Cover.

Plant:

*Form.*—Vigorous, young plants are compact, at first they are upright and in the second year they are spreading, and at maturity they are compact, spreading, and dense.

*Height.*—Approximately 80 cm on average.

*Width.*—Approximately 70 cm on average.

Branches:

*Color.*—Young stems: reddish bronze with a smooth surface. Adult wood: green with a smooth surface.

*Thorns.*—Size: medium, approximately 5 mm in length on average, slightly curved downward on the upper surface, and concave on the under surface. Position: irregular. Color: initially light red-brown, and changing to red with maturity. Quantity: typical for a Ground Cover rose plant.

Leaves:

*Stipules.*—Green in coloration.

*Leaflets.*—Number: commonly 5 and 7. Configuration: Generally elongated, pointed apex, and commonly slightly curved upwards thereby giving the leaflets a partially closed appearance. Quantity: very abundant. Size: Commonly approximately 25 mm in length on average, and approximately 15 mm in width on average. Serration: slightly serrate. Color: (young foliage): Upper surface: green. Under surface: lighter green than upper surface. Color: (adult foliage): Upper surface: green and very glossy. Under surface: lighter green than upper surface and matte. General appearance: dense, green foliage that is glossy on the upper surface and matte on the under surface with the curled nature of the leaves being readily apparent. Texture: leathery. Stipules: Green in coloration.

Inflorescence:

*Number of flowers.*—In clusters of flowers as a large spray.

*Peduncle.*—Directly under buds and flowers commonly is reddish bronze in coloration and commonly changing to a soft green coloration at a more distant location.

*Sepals.*—Shape: commonly extend beyond the petals of the bud, and pointed in configuration.

*Buds.*—Color when opening: strong bright red-purple, Red-Purple Group 57A.

*Flower.*—Form: somewhat flattened on the upper side, and convex on the under side. Appearance: smooth on both petal surfaces. Diameter: approximately 6.5 cm on average. Color (when opening begins): Upper surface: predominantly Red-Purple Group 57A. Color (when blooming): Upper surface: predominantly Red-Purple Group 57A. The bright yellow coloration of the pollen and the reproductive organs commonly is visible at the center. Under surface: predominantly Red-Purple Group 57A. Color (at the end of opening): Upper surface: predominantly Red-Purple Group 57A. Under surface: predominantly Red-Purple Group 57A. Basal petal spot: near White Group 155B on both surfaces. Fragrance: none. Heat resistance: very good. Lasting quality: very good. Petal form: broad, and reflexed. Petal size: approximately 24 mm in length on average, and approximately 20 mm in width on average. Petal number: commonly approximately 15 on average. Petal arrangement: generally arranged in a regular pattern with overlapping petal edges. Petal drop: good with the petals detaching cleanly upon fully maturity. Stamens: Regularly arranged around the styles. Filaments: yellow in coloration. Pollen: yellow in coloration. Stigmas: yellow in coloration. Styles: thin, regularly arranged at the center, and tend to be of substantially the same length. Hips: None observed during observations to date.

Development

*Vegetation.*—Strong, compact, and vigorous.

*Blooming.*—Abundantly in large sprays particularly late to very late in the season.

*Aptitude to bear fruit.*—None.

*Winter hardiness.*—Good.

*Resistance to diseases.*—Excellent with respect to Blackspot, Powdery Mildew, Downey Mildew, and Rust.

I claim:

1. A new and distinct Ground Cover Rose plant characterized by the following combination of characteristics:

(a) forms in sprays attractive long-lasting red-purple blossoms which are lacking in fragrance with yellow pollen and reproductive organs commonly being visible at the center and which commonly display very good heat resistance and color stability upon aging, (b) exhibits a dense, compact, and spreading growth habit, (c) abundantly forms attractive very glossy foliage that contrasts well with the red-purple blossoms wherein the surfaces of the leaflets commonly are somewhat curled and partially closed, (d) exhibits excellent disease resistance with respect to Blackspot, Powdery Mildew, Downey Mildew, and Rust, and (e) is particularly well suited for growing as attractive ornamentation in the landscape;

substantially as illustrated and described.

* * * * *